(12) United States Patent
Venkataraman et al.

(10) Patent No.: US 7,645,801 B2
(45) Date of Patent: Jan. 12, 2010

(54) REDUCED IRRITANT ENEMA FOR TREATMENT OF INFLAMMATORY BOWEL DISEASE (IBD)

(75) Inventors: Bala Venkataraman, Alpharetta, GA (US); Lindsey Brown, Atlanta, GA (US); Daxa Patel, Marietta, GA (US)

(73) Assignee: Alaven Pharmaceutical LLC, Marietta, GA (US)

( * ) Notice: Subject to any disclaimer, the term of this patent is extended or adjusted under 35 U.S.C. 154(b) by 69 days.

(21) Appl. No.: 11/749,732

(22) Filed: May 16, 2007

(65) Prior Publication Data

US 2008/0183142 A1    Jul. 31, 2008

Related U.S. Application Data

(60) Provisional application No. 60/898,072, filed on Jan. 29, 2007.

(51) Int. Cl.
A01N 33/02    (2006.01)
A01N 33/18    (2006.01)

(52) U.S. Cl. ...................... 514/646; 514/741
(58) Field of Classification Search .................. 514/646, 514/741
See application file for complete search history.

(56) References Cited

U.S. PATENT DOCUMENTS

| | | | |
|---|---|---|---|
| 2,647,853 A | 8/1953 | Lardé et al. | |
| 3,088,870 A | 5/1963 | McDermott | |
| 4,150,744 A | 4/1979 | Fennimore | |
| 4,211,777 A | 7/1980 | Chambers | |
| 4,440,763 A | 4/1984 | Lover | |
| 4,455,305 A | 6/1984 | Rokos | |
| 4,540,685 A | 9/1985 | Bauer | |
| 4,632,921 A | 12/1986 | Bauer | |
| 4,657,900 A | 4/1987 | Powell et al. | |
| 4,664,256 A | 5/1987 | Halskov | |
| 4,699,902 A | 10/1987 | Bauer | |
| 4,837,229 A | 6/1989 | Rokos et al. | |
| RE33,239 E | 6/1990 | Halskov | |
| 5,010,069 A | 4/1991 | Bottom et al. | |
| 5,082,651 A | 1/1992 | Healey et al. | |
| 5,120,306 A | 6/1992 | Gosselin | |
| 5,270,337 A * | 12/1993 | Graf | 514/499 |
| 5,352,681 A | 10/1994 | Wittebrood et al. | |
| 5,378,470 A | 1/1995 | Lahr | |
| 5,449,520 A | 9/1995 | Frigerio et al. | |
| 5,529,833 A * | 6/1996 | Speer et al. | 428/215 |
| 5,668,123 A | 9/1997 | Berry | |
| 5,716,648 A | 2/1998 | Halskov et al. | |
| 5,725,872 A | 3/1998 | Stamm et al. | |
| 5,731,302 A | 3/1998 | Farolfi et al. | |
| 5,747,477 A | 5/1998 | Carceller et al. | |
| 5,843,482 A | 12/1998 | Rhodes et al. | |
| 6,326,364 B1 | 12/2001 | Lin et al. | |
| 6,699,894 B1 | 3/2004 | Earle et al. | |
| 7,312,243 B1 | 12/2007 | Pravda | |
| 2005/0159396 A1 | 7/2005 | Harty | |
| 2006/0076536 A1 * | 4/2006 | Barshied | 252/188.28 |
| 2006/0141057 A1 | 6/2006 | Harty | |
| 2006/0183804 A1 | 8/2006 | Brinkman et al. | |
| 2006/0223787 A1 | 10/2006 | Devane et al. | |
| 2006/0264409 A1 | 11/2006 | Harty | |
| 2006/0270635 A1 | 11/2006 | Wallace et al. | |
| 2007/0043004 A1 | 2/2007 | Jepsen | |
| 2007/0066578 A1 | 3/2007 | Shimizu | |
| 2007/0084144 A1 | 4/2007 | Labrecque et al. | |

FOREIGN PATENT DOCUMENTS

| | | |
|---|---|---|
| CA | 2274943 | 12/1999 |
| EP | 0398207 | 5/1989 |
| EP | 1312368 | 8/2005 |
| JP | 403047161 | 5/1990 |
| WO | WO 2005107479 A1 * | 11/2005 |

OTHER PUBLICATIONS

Food Additives "Know What's In Your Food And Why It's There".*
Bondesen et al. "*Aminosalicylic-Acid Enemas in Patients With Active Ulcerative Colitis Influence of Acidity on the Kinetic Pattern*" Abstract. Scandinavian Journal of Gastroenterology 19 (5) 677-682 (1984).
Yokoyama et al. "*Efficacy of Weekend 5-ASA (Mesalazine) Enema as a Maintenance Therapy in Patients With Ulcerative Colitis: A Randomized Controlled Study*" Abstract. Gastroenterology 130 (4, Suppl.2): A480 (Apr. 2006).
Hui et al. "*Pharmacokinetics of 5AQSA (M) and N-acetyl-5-asa (NM) after Single and Multiple Doses of 5-ASA Rectal Enema (4 and 1 GM/60 ML) and Oral Sulfasalazine (SF)*" Abstract. Pharmaceutical Research (NY) 11 (10 Suppl.): S442 (1994).
Fitzgerald et al. "*Mesalamine in Ulcerative Colitis*" Abstract. DCIP 1991 Feg; 25(2): 140-5.
D'Albasio et al. "*Intermittent Therapy With High-Dose 5-Aminosalicylic Acid Enemas for Maintaining Remission in Ulcerative Proctosigmoiditis*" Abstract. Dis Colon Rectum. May 1990; 33(5): 394-7.
Ginsberg et al. "*Treatment of Left-sided Ulcerative Colitis With 4-Aminosalicylic Acid Enemas. A Double-Blind, Placebo-Controlled Trial*" Abstract. Ann Intern Med. Feb. 1988; 108(2): 195-9.

(Continued)

Primary Examiner—Sreeni Padmanabhan
Assistant Examiner—Renee Claytor
(74) Attorney, Agent, or Firm—Thompson Hine LLP; Ashish D. Patel

(57) ABSTRACT

The present invention comprises packaged enemas for the treatment of Inflammatory Bowel Disease (IBD), having substantially pure 5-ASA as the active ingredient, with a liquid carrier medium having a material avoidance of bowel irritant substances, such as anti-oxidants for the 5-ASA active ingredient, including such sulfites as potassium metabisulfite, for example, and contained within a sealed and substantially oxygen-free barrier package, which may preferably be formed of a foil/polymer laminate, and which package contains or otherwise includes an oxygen scavenger, such as a an oxygen scavenging sachet.

18 Claims, No Drawings

OTHER PUBLICATIONS

Henderson et al. "*Stability of Mesalamine In Rectal Suspension Diluted With Distilled Water*" Abstract. L8 Answer 4 of 7 DDFU. Am.J.Hosp.Pharm. (51, No. 23, 2955-57, 1994) 1 Tab. 9 Ref.

Buul et al. "*Retrograde Spread of Pentasa R Enema in 24 Patients With Colitis*" Abstract. Answer 6 of 7 DDFU. Gastroenterology (96, No. 5, Pt 2, A523, 1989) 1 Ref.

Bondesen et al. "*Aminosalicylic-Acid Enemas in Patients With Active Ulcerative Colitis Influence of Acidity in the Kinetic Pattern*" Abstract. Accession No. PREV198579024784; Published by: Scandinavian Journal of Gastroenterology 19 (5): 677-682 (1984).

Eliakim et al., "*Clinical Trial On the Efficacy and Tolerability of a Novel Low-Volume Mesalamine Foam (2xlg 5-ASA/30ml) Vs Mesalamine Foam (2xlg 5-ASA/60ml)in Active Ulcerative Proctitis or Proctosigmolditis*" Abstract T1132. published in AGA Abstracts (A-481).

Thabane et al., "*Rectal 5 ASA to Maintain Remission of Distal Ulcerative Colitis (UC): a Cochrane Collaboration Meta-Analysis*" Abstract M1113 published in AGA Abstracts (A311).

Mottet et al., *Which Treatments are Appropriate for Acute or Steroid-Refractory/Dependent Crohn's Disease? A Multidisciplinary European Expert Panel* Abstract M1116. published in AGA Abstracts (A312) (*EPACT*)(A311).

TEVA Pharmaceuticals USA (Sellersville, PA 18960) Mesalamine Rectal Suspension, USP: (i) TEVA packaging for Mesalamine Rectal Suspension, USP 4g/60 mL, (ii) Photograph image of packaging for Mesalamine Rectal Suspension, USP 4g/60 mL, and (iii)Informational drug data sheet for Mesalamine Suspension—Daily Med; http://dailmed.nlm.nih.gov/dailymed/drugInfo.cfm?id=2357.

Pharma, Dr. Falk GmBH. Public Assessment Report: "*Mutual Recognition Procedure: Salofalk 1g/Actuation rectal foam*" UK reference No. UK/H/0527/0001/E001; UK License No. PL 08637/0003; 1-38.

[No Author] Product Information Brochure: "*Salofalk® MesalazineFoam Enema*" Orphan Australia Pty.Ltd.

[No Author] Leaflet: "*Salofalk® Enemas Mesalazine*" Consumer Medicine Information; 1-5.

Magee et al. "*Associations Between Diet And Disease Activity In Ulcerative Colitis Patients Using A Novel Method Of Data Analysis*" Article. Nutrition Journal (2005) 4:7.

Mulder et al. "*Comparison of 5-Aminosalicylic Acid (3) and Prednisolone Phosphate Sodium Enemas (30 mg) in the Treatment of Distal Ulcerative Colitis*" Article. Scandinavian Journal Gastroenterol, 23, 1005-1008 (1988).

\* cited by examiner

REDUCED IRRITANT ENEMA FOR TREATMENT OF INFLAMMATORY BOWEL DISEASE (IBD)

PRIORITY CLAIM

To the fullest extent permitted by law, the present non-provisional patent application claims priority to, and the full benefit of, U.S. Provisional Patent Application Ser. No. 60/898,072, filed on Jan. 29, 2007, and entitled "Composition and Method for Treating Inflammation of the Large Intestine".

TECHNICAL FIELD

The present application relates generally to the enema arts, more particularly to enemas for the treatment of inflammatory bowel disease (IBD), and yet more particularly to such IBD treatment enemas utilizing 5-aminosalicylic acid (5-ASA), but possessing substantially reduced bowel irritation properties.

BACKGROUND OF THE INVENTION

Inflammatory bowel disease (IBD) comprising Crohn's disease and ulcerative colitis, has been estimated to afflict more than 2 million Americans. Unfortunately, a permanent cure of these IBD and related diseases has not been found. However, certain treatments, when properly utilized, will substantially reduce the symptoms thereof. Among these preferred treatments for IBD are preparations containing 5-ASA, and/or its precursor molecules, which may be molecularly split by the intestinal flora to produce in situ the 5-ASA treatment molecule.

Various means of carrying and administering effective medicants ultimately to the afflicted bowel areas have been developed, and include, inter alia, oral administration, suppositories, and enemas, for example. However, each of these delivery methodologies have had certain disadvantages and/or deficiencies associated therewith.

For example, oral administration of the 5-ASA molecule, usually in solid form, generally may require a higher dosage of the 5-ASA active agent, because of the effect of gastric juices thereon as the oral dosage passes through the digestive process. In order to reduce the negative influence of gastric juices upon oral doses, such orally administered medicants generally have been enterically coated, and/or have been delivered by an enteric feeding tube. Examples of oral dosage systems utilizing 5-ASA treatment include U.S. Pat. No. 2,647,853 to Lardé et al., U.S. Pat. No. 4,540,685 to Bauer, U.S. Pat. No. 4,632,921 to Bauer, U.S. Pat. No. 4,699,902 to Bauer, U.S. Pat. No. 5,120,306 to Gosselin, United States Publication No. 2006/0223787 A1 to Devane et al., United States Publication No. 2006/0264409 A1 to Harty, United States Publication No. 2007/0043004 A1 to Jepsen, and United States Publication No. 2007/0066578 A1 to Shimizu.

Suppository utilizations of 5-ASA have generally utilized 5-ASA in the solid form, or in greatly concentrated form for containment within a dissolvable suppository as inserted into the rectum. However, given the relatively low volume of such a suppository, sufficient spreading of the 5-ASA active agent to the areas of the bowel afflicted by IBD has been a continuing problem with the suppository methodology. Examples of the suppository treatment vehicle for 5-ASA include U.S. Pat. No. 4,540,685 to Bauer, U.S. Pat. No. 4,632,921 to Bauer, U.S. Pat. No. 4,699,902 to Bauer, U.S. Pat. No. 5,449,520 to Frigerio et al., and U.S. Pat. No. 5,082,651 to Healey et al.

Generally speaking, enema formats for treatment of inflammatory bowel diseases have had the substantial utility of possessing the ability to deliver a substantial volume of 5-ASA as contained within a treatment vehicle and with such application directly to the areas of the bowel afflicted by IBD. Such enemas have included foam enemas and liquid enemas. As for foam enemas, the disadvantage of a relatively low density of the foam necessarily results in difficulties of administering substantial and accordingly therapeutic amounts of the 5-ASA active agent to the appropriate portions of the bowel requiring treatment. Indeed, foam enemas have long experienced difficulties in penetrating all areas of the bowel, including such areas as the ascending colon. Certain foam references include U.S. Pat. No. 5,725,872 to Stamm et al., U.S. Pat. No. 5,449,520 to Frigerio et al., U.S. Pat. No. 5,082,651 to Healey et al., and European Patent No. 1312368 to Kühn.

Hence, the liquid enema format possesses certain advantages not present in oral treatment, suppositories, or foam enemas, in that liquid enemas have simultaneously both sufficient volume and density for the required penetration to the entirety of the bowel, and thus facilitate treatment of the entirety thereof. One example of liquid enemas having substantial medical and commercial success are those disclosed and described in U.S. Pat. No. 4,657,900 to Powell et al., issued on Apr. 14, 1987, and entitled "Pharmaceutical Article of Manufacturer Comprising a Bi-Sulfite Stabilized Aqueous Solution of 5-Amino Salicylic Acid and Method", and owned in common with the assignee hereof. The 5-ASA compositions set forth in U.S. Pat. No. 4,657,900 to Powell et al. have been marketed under the trademark Rowasa® by Solvay Corporation and the assignee hereof, and of which the present invention constitutes a substantial improvement thereover. Accordingly, the teachings of U.S. Pat. No. 4,657,900 to Powell et al., are incorporated by reference herein.

As set forth in the Powell et al. patent, the enema compositions thereof are stabilized against oxidation (and thus decomposition, discoloration and reduction in efficacy) of the 5-ASA active agent by the inclusion of sulfite compounds (i.e., bisulfites, metabisulfites, etc.), which provide the enema composition with a substantial shelf-life upon prolonged storage. However, certain disadvantages, and in particular colon/bowel irritation, have been associated with such stabilizing sulfite compounds. Accordingly, the reduction and/or elimination of bowel irritating compounds, such as, for example, sulfite compounds and/or other antioxidants for the 5-ASA active agent, that albeit are necessary for stabilization, has been long since deemed beneficial, but until the present invention has not been successfully accomplished.

One example of attempts to compete with the present assignee's prior Rowasa® commercial embodiment of the compositions and methods set forth in U.S. Pat. No. 4,657,900 to Powell et al., has been enemas produced and distributed by Teva Pharmaceuticals USA of Sellersville, Pa. 18960, and constitutes a liquid enema product (FDA approved in 2004) for the treatment of IBD. However, the Teva Liquid Enema 5-ASA product, as approved approximately 17 years after the issuance of the Powell et al. patent, continues to contain the bowel irritating bisulfite stabilizer. The Teva product insert is dated "Revised: 11/2006" and states in regard to the bisulfite compounds:

"WARNINGS Mesalamine rectal suspension USP contains potassium metabisulfite, a sulfite that may cause allergic-type reactions including anaphylactic symptoms and life-threatening or less severe asthmatic episodes in certain susceptible people. The overall prevalence of sulfite sensitivity in the general population is unknown but probably low.

Sulfite sensitivity is seen more frequently in asthmatic or in atopic nonasthmatic persons. Epinephrine is the preferred treatment for serious allergic or emergency situations even though epinephrine injection contains sodium or potassium metabisulfite with the above-mentioned potential liabilities. The alternatives to using epinephrine in a life-threatening situation may not be satisfactory. The presence of a sulfite(s) in epinephrine injection should not deter the administration of the drug for treatment of serious allergic or other emergency situations."

Accordingly, and as recognized by the competitors in the relevant art marketplace, reduction in bowel irritating stabilizers/anti-oxidants for the 5-ASA active ingredient, such as, for example, potassium metabisulfite, has been desirable for an extended period of time comprising at least 20 years, but has not been successfully accomplished until the present invention.

Therefore, it is readily apparent that there is a need for enema compositions and methods for treating inflammation of the large intestine, in particular the rectum, sigmoid colon, and the descending colon, that avoids the side effects associated with the bowel irritating sulfite compounds and other antioxidants for the 5-ASA active ingredient of known enema compositions, yet provides for a substantial shelf-life upon prolonged storage.

BRIEF SUMMARY OF THE INVENTION

Briefly described, in a preferred embodiment, the present invention overcomes the above-mentioned disadvantages, and meets the recognized need for such an invention by providing an enema composition for the treatment of inflammatory bowel disease, which enema composition materially avoids the inclusion of bowel irritant substances, such as anti-oxidants for the 5-ASA active ingredient, including sulfite compounds, yet, via the present inventive packaging structure and method, exhibits a substantial shelf-life upon prolonged storage.

More specifically, the present invention is directed to packaged individual, or "single-use", enemas for the treatment of inflammatory bowel disease (IBD). The inventive enemas of the present invention comprise an effective and stable dosage suspension of substantially pure 5-ASA, as the active ingredient. The 5-ASA is contained within a substantially oxygen-free liquid carrier medium, as preferably prepared by nitrogen purge and vacuum techniques known to those skilled in the art, and packaged and sealed thereafter within a nitrogen atmosphere via a form, fill and seal machine (which such packaging and sealing processes further advantageously capture nitrogen gas with the sealed package/pouch), also known to those skilled in the art. Significantly, the liquid carrier medium has a material avoidance of bowel irritant substances, such as anti-oxidants for the 5-ASA active ingredient, including such sulfites as potassium metabisulfite, for example.

The dosage suspension is contained within an application bottle, which is preferably pre-formed of a polymeric material and having sufficient flexibility/malleability for ease of use by an unassisted patient. The application bottles are contained within a sealed and substantially oxygen-free barrier package which may preferably be formed of a foil/polymer laminate, as described more completely, infra. The oxygen-free barrier package may, in preferred embodiments, be presented in the form of a pouch, and further contains an oxygen scavenger therein, which in some preferred embodiments may be in the form of oxygen scavenging sachet.

Among the several resulting benefits of the compositions and methods of the present invention is the advantage of providing a barrier package sufficient to prevent migration of oxygen thereinto, and accordingly into the application bottles that contain the dosage suspension, and with the beneficial result of permitting an extended shelf-life upon prolonged storage, while simultaneously avoiding the inclusion of bowel irritant substances within the treatment enema.

Yet additionally, the barrier package, in combination with the oxygen scavenging sachet, and in further addition to the nitrogen gas concomitantly sealed within the package during the package sealing process (i.e., occurring under nitrogen atmosphere), sufficiently and effectively prevents oxidation of the present sulfite/antioxidant-free 5-ASA enema compositions and, thus, enables the long-term stability and shelf-life of same.

These and other features and advantages of the invention will become more apparent to one skilled in the art from the following description and claims.

DETAILED DESCRIPTION OF PREFERRED AND EXEMPLARY EMBODIMENTS

In describing the preferred and selected alternate embodiments of the present invention, specific terminology is employed for the sake of clarity. The invention, however, is not intended to be limited to the specific terminology so selected, and it is to be understood that each specific element includes all technical or compositional equivalents that operate or perform in a similar manner to accomplish similar functions. Additionally, and as indicated supra, the teachings and disclosure of U.S. Pat. No. 4,657,900 to Powell et al., are entirely incorporated by reference herein.

Broadly stated, the present invention in its preferred form is a packaged single-use enema for the treatment of inflammatory bowel disease and related conditions, comprising an effective and stable dosage suspension of substantially pure 5-ASA contained within a substantially oxygen-free liquid carrier medium having a material avoidance of a substantial bowel irritant. The specific composition of the enema is described more fully hereinbelow.

As also more fully described below, application bottles containing the effective dosage suspension are preferably prepared (via known pre-fill nitrogen purging and vacuum techniques), packaged and sealed under a nitrogen (or other substantially inert gas) atmosphere within a substantially oxygen-free barrier package. Preferably included within the package, in isolation from or in communicating disposition with the application bottles thereof, is an oxygen scavenger, preferably in the form of an oxygen scavenging sachet.

As such, and in addition to the nitrogen gas concomitantly sealed within the package during the package sealing process (i.e., occurring under nitrogen atmosphere), the barrier package sufficiently and effectively prevents migration of oxygen thereinto and into the dosage suspension of the application bottles upon prolonged storage thereof. Manifestly, discoloration, damage and reduced efficacy of the 5-ASA active ingredient in the present enema composition is effectively avoided and, instead, the efficacy and medicinal potency of the 5-ASA enema is maintained, all with the material avoidance or exclusion of bowel irritating antioxidants for the 5-ASA active ingredient, such as sulfite compounds (e.g., potassium metabisulfite).

Preferably, the present inventive dosage suspension and associated method of treatment of human colonic conditions comprise the steps of administering intra-colonially an effective amount of a treatment dose comprising approximately 1 to approximately 4 grams of 5-ASA in approximately 20 to approximately 60 milliliter suspension matrix. The suspension matrix further preferably comprises one or more of potassium acetate (as a buffering agent), carbomer (as a thickening agent to adjust viscosity of the enema composition), EDTA (as a chelating agent), sodium benzoate (as an antimicrobial), xanthan gum (to adjust viscosity), and purified water, and with the material avoidance of colonic irritants, such as, for example, sulfite compounds and other irritant-inducing antioxidants for the 5-ASA active ingredient.

Notably, and as described more fully hereinbelow with reference to the many examples, the present invention contemplates numerous preferred embodiments of the instant enema composition, wherein the amounts of each specific ingredient, in any varying combination, may be appropriately selected based upon the treatment measures, protocols and/or other diagnostics relevant to the targeted patient populace. Accordingly, and as more fully described hereinbelow, the amounts and type of each specific ingredient, in any varying combination, are only exemplary preparations of the present composition and, thus, are not intended to so limit the multitude of combinations attainable from the present invention. It is also to be understood that as used in the specification and in the claims, "a" or "an" can mean one or more, depending upon the context in which it is used.

The following Examples I-IV are illustrative of various preferred and alternative embodiments of the present enema composition, each which preferably include approximately 4 grams of 5-ASA within a volume of approximately 60 ml of a carrier liquid, and with the material avoidance of any bowel/colonic irritant substances, such as anti-oxidants for the 5-ASA active ingredient, including sulfites such as potassium metabisulfite, for example. Additionally, and although more fully described hereinbelow, the present enema compositions of each of the following Examples are preferably processed, packaged and maintained in a substantially oxygen-free environment, such as for example initially by means of nitrogen gas flushing/vacuum process and a nitrogen gas atmosphere during filling, according to techniques and methods known to those of ordinary skill in the relevant art, and thereafter by means of the specialized packaging structure and methods of the present invention, which include, within the packaging structure, oxygen scavengers in the form of, for example, oxygen-scavenging sachets.

EXAMPLES

The mixture methodology of certain preferred and alternate embodiments of the present enema composition, as set forth in Examples I-IV, infra, may utilize the following generally-described procedures in connection with the lists of formulation ingredients:

Premix the carbomer, potassium acetate, xanthan gum and Mesalamine (i.e., 5-ASA) according to known techniques and in a low shear mixer (such as, for example, within a Marion Mixer) for a relatively short period of approximately 10-60 minutes. Discharge the contents into a sealed container to form a premix. Take this premix, along with purified water, EDTA and sodium benzoate and charge into a high sheer mixer (such as, for example, a Lee processor preferably with an associated countersweep apparatus) and mix for approximately 2-4 hours. Vacuum and nitrogen gas purges are preferably utilized in some preferred embodiments throughout this process to avoid and/or reduce the amount of oxidation that otherwise may occur. Transfer the contents into a sealed tank. Verify the pH (preferably at approximately 3 to approximately 5, and more preferable approximately 3.5 to approximately 5) and the viscosity of approximately 200-500 cps. The contents of the sealed tank (which may, in certain preferred embodiments, be required to be maintained under positive nitrogen gas pressure) are pulled using a sine pump into a tank, and a 30-40 mesh in-liner strainer may be used between the sealed tank and the sine pump. The contents of the tank are pumped into the enema container filling machine. The enema container or bottle is preferably nitrogen purged prior to being filled, wherein after being filled with the enema composition, a nitrogen gas blanket is applied prior to bottle capping. An oxygen scavenger sachet may preferably be enclosed into the enema tray in some preferred embodiments prior to pouching under a nitrogen gas blanket.

Example I

The following formulations are utilized in some preferred and alternative embodiments, and manufactured according to the procedures set forth supra:
  4.094 g 5-ASA (Mesalamine)
  0.045 g of Carbomer
  0.247 g of Potassium Acetate
  0.15 g of Xanthan Gum
  Per 60 ml. Purified Water
  0.06 g of Sodium Benzoate
  0.06 g of Edetate Disodium
  QS with Purified Water Example II The following formulations are utilized in some preferred and alternative embodiments, and manufactured according to the procedures set forth supra:
  4.023 g 5-ASA (Mesalamine)
  0.045 g of Carbomer
  0.247 g of Potassium Acetate
  0.15 g of Xanthan Gum
  Per 60 ml. Purified Water
  0.06 g of Sodium Benzoate
  0.06 g of Edetate Disodium
  QS with Purified Water Example III The following formulations are utilized in some preferred and alternative embodiments, and manufactured according to the procedures set forth supra:
  4.094 g 5-ASA (Mesalamine)
  0.045 g of Carbomer
  0.247 g of Potassium Acetate
  0.15 g of Xanthan Gum
  Per 60 ml Purified Water
  0.03 g of Sodium Benzoate
  0.06 g of Edetate Disodium
  QS with Purified Water Example IV The following formulations are utilized in some preferred and alternative embodiments, and manufactured according to the procedures set forth supra:
  4.094 g 5-ASA (Mesalamine)
  0.045 g of Carbomer
  0.247 g of Potassium Acetate
  0.15 g of Xanthan Gum
  Per 60 ml Purified Water
  0.06 g of Sodium Benzoate
  0.06 g of Edetate Disodium
  QS with Purified Water The examples presented supra are intended to serve as exemplary, although preferred, preparations of the present composition and, thus, are not intended to so limit the multitude of combinations attainable from the present invention.

Preferably, and in reference now to the preferred containment and packaging structures and procedures of the present invention, the dosage suspension prepared by way of the foregoing examples or otherwise (e.g., see Product Study described infra) is contained within an application bottle, which is preferably pre-formed of a polymeric material, and which preferably comprises sufficient flexibility/malleability for ease of use by an unassisted patient. Such polymeric materials may include, without limitation polyethylene, polypropylene, polyolefin, or the like.

Prior to filling the application bottle with the present enema composition, the application bottle preferably undergoes a nitrogen (or other inert gas) purging and vacuum process to sufficiently expel or otherwise pull and evacuate oxygen gas from therewithin. Thereafter, and under continued nitrogen (or other inert gas) atmosphere, the bottle applicator/cap is preferably securely engaged to the bottle, whereupon the bottle may proceed to the packing/pouching and sealing stage, also carried out under nitrogen (or other inert gas) atmosphere, as described more fully hereinbelow. Such bottle nitrogen purging/vacuum processes, and subsequent form, fill and sealing processes implemented under nitrogen atmosphere (i.e., referred to as nitrogen blankets), are known to those skilled within the art, and may, where applicable, be performed on available form, fill and seal machines, or other specialized machinery, including bottle pack machines which include bottle moulding, suspension filling and bottle sealing.

Yet additionally, the present invention further contemplates, in preferred embodiments, that such nitrogen purging processes may further be implemented via bubbling nitrogen gas through the present enema composition prior to bottling same, whilst applying the requisite vacuum conditioning thereover, according to processes known to one skilled within the art. Such bubbling processes may be implemented in addition to, or in lieu of, nitrogen purging/vacuum of the application bottle prior to filling same with the nitrogen purged/bubbled enema composition.

Wherefore, a significant functional portion of the present invention comprises the sealed substantially oxygen-free barrier package for containing therein the prepared application bottles, described supra. Specifically, the application bottles are contained within a sealed and substantially oxygen-free barrier package which may preferably be formed of a foil/polymer laminate. The structure of the oxygen barrier package comprises, in preferred embodiments, a polyester/aluminum foil/linear low density polyethylene (LLDPE) composite substrate, and which may preferably be laminated together by the use of at least one compatible adhesive. Accordingly, and more particularly, the preferred oxygen barrier package comprises a composite film structure of polyester/adhesive/aluminum foil/adhesive/LLDPE, the specifics of which are described more fully hereinbelow. Yet additionally, the oxygen-free barrier package may, in preferred embodiments, be presented in the form of a pouch.

More specifically, and in preferred embodiments of the invention hereof, the oxygen barrier composite substrate or film is available from Outlook Group Corporation of Neenah, Wis. 54956, is preferably approximately 3.4 milliliters thick, and comprises a polyester material (0.00048"), which is preferably produced by DuPont Corporation under the trademark "Mylar LBT-2", and which may be preferably treated by corona discharge on the sides thereof. The aluminum foil component (0.0007") is preferably a "Reynolds 1235-0 alloy", which may be utilized preferably in unprinted form. Alternatively, aluminum foils from AJ Oster Foils, and designated as "1145-0 alloy" may be utilized as for alternatives for the aluminum foil component. Alternate and suitable linear low density polyethylenes (LLDPE) (0.002") may be obtained from DuPont Corporation under the trademark Sclairfilm SL-1®.

Under the Outlook Group Corporation test method 400-53, the coefficient of film-to-metal has been measured at 0.35+/−0.5, and the film-to-film coefficient of friction has been measured under the Outlook Group Corporation test method 400-32 at 0.50+/−0.05. The adhesive (0.00025") utilized in preferred embodiments of the laminates hereof is available from Rohm & Haas, Philadelphia, Pa. 19106, as Adcote® 532A/Coreactant 532B.

Possible alternative packaging films may include: (1) SPI Barrier Film x9624-00x (available from SPI Supplies of West Chester, Pa. 19380) using the Sig Linium 303 Wrapper, and (2) Pechiney form/fill/seal Barrier Film NXEHW80 (0.008") (available from Pechiney Packaging Plastic, Inc. of Chicago, Ill. 60631) using the Multivac R230 form/fill/seal.

As described supra, the prepared application bottles are preferably packaged and sealed within the preferred package/pouch under nitrogen (or other inert gas) atmosphere, utilizing machinery and methods (i.e., form, fill and seal) known to one of ordinary skill within the art. As such, and as an advantageous result of such packaging and sealing conditions, nitrogen gas is concomitantly sealed within the package/pouch during the package/pouch sealing process, which, in addition to the barrier package and oxygen scavenging sachet (described infra), sufficiently and effectively prevents oxidation of the present sulfite/antioxidant-free 5-ASA enema compositions and, thus, enables the long-term stability and shelf-life of same. Although the present invention does contemplate, in an alternate embodiment, that sealing of the package/pouch may be accomplished in the absence of a nitrogen atmosphere, but with the material inclusion of an oxygen scavenging sachet, the most preferred method of packaging and maintaining the present sulfite-free/antioxidant-free enema compositions contemplates the application of such a nitrogen atmosphere (for nitrogen gas trapping within the package) and a preferred oxygen scavenging sachet (see also Product Study, infra).

As a yet additional safeguard against oxidation of the present sulfite-free/antioxidant-free enema compositions, and in the preferred embodiment of the invention, the oxygen-free barrier package/pouch further comprises an oxygen scavenger contained therein, which in some preferred embodiments may be in the form of a sachet. In particular, the sachet may be loosely disposed within the preferred packaging hereof, affixed to an inner surface of the preferred packaging, integrally formed (as a laminate or otherwise) with the preferred packaging substrate, disposed within the cap or lid of the application bottle, disposed on or otherwise affixed to any portion of the application bottle, including the sidewalls and/or bottom thereof, and/or combinations of the foregoing. Such oxygen scavenging sachets are available from Multisorb Technologies, Inc. of Buffalo, N.Y. 14224 (e.g., "large" oxygen scavenger, Frespax, D-200, part#02-01403CG05; or, "small" oxygen scavenger, Freshpax, D-100, part#02-01403CG04).

Indeed, the present invention further contemplates that such an oxygen scavenging sachet can be disposed or otherwise formed over any portion of the inner and/or outer surface of the package/pouch, and/or over any portion of a retaining tray in which the application bottles may be placed or "seated" once disposed within the package/pouch (e.g. layered within the bottle recesses of the tray). Yet additionally, the oxygen scavenger may be in the form of a pouch, wrap or sleeve that may encircle, enclose or otherwise encompass all or a portion of the application bottle(s).

Product Study

A study was conducted to evaluate the stability or shelf-life of the present sulfite-free enema composition (i.e., antioxidant-free, and in particular, potassium-metabisulfite-free enema composition), as contained within the packaging structure and components described hereinabove. The enema composition manufacture/formulation, subsequent packaging tests and structures, and associated stability test results are as follows:

Manufacturing/Formulation:
1. Equipment used: 20 L SS Tank, Lighthin Mixer Model MSU-1500x2 Mixer #1 & Mixer #2, Ross Mixer Mill and 20 L are checked for cleanliness.
2. Charge 11.6 L of purified water to a 20 L stainless steal tank.
3. Add 16.4 g sodium benzoate to Step #2 and dissolve using Model MSU-1500 Lighthin Mixer.
4. Slowly add 12.3 g carbomer 934P (Internal) to Step #3 while mixing, set the timer and mix with a vortex for two hours (+/−5 minutes) using the Model MSU-1500 Lighthin Mixer.
5. Cover tightly and allow to stand overnight at room temperature.
6. Mill Step #5 for 20 minutes using Ross Mixer TS61201-00. Let deaerate for 3 hours, no $N_2$ bubble.
7. Add 16.4 g disodium EDTA to Step #6, mix without a vortex for 30 minutes using Model MSU-1500 Lighthin Mixer.
8. Pre-blend 41.0 g xanthan gum and 67.3 g potassium acetate for 2-3 minutes or until a uniform mixture is achieved.
9. Slowly add xanthum gum and potassium acetate preblend to Step #8 while mixing without a vortex. Mix without a vortex for two hours or until xanthum gum is dissolved.
10. Charge 1115.9 g Mesalamine (5-ASA) into a 20 L stainless steel tank. Add 2707 g water. Document actual amount of water used.
11. Slurry Step #11 using Lighthin Mixer Model MSU-1500 until smooth slurry.
12. Add Mesalamine (5-ASA) slurry Step #12 to the batch, set the timer and mix without a vortex for 30 minutes (+/−2 Minutes) using the Model MSU-1500 Lighthin Mixer.
13. QS to 16 L with purified water and mix without a vortex for 30 minutes (+/−2 minutes) using model MSU-1500 Lighthin mixer.
14. Mill Step #14 using Ross Mixer TS61201-00 for 30 minutes (+/−2 minutes) at 3500 RPM, for resulting enema solution.

Bottling:
1. Bubble enema solution with $N_2$ in a hood for 5 hours.
2. Pull 25 in Hg overnight in VAC Desiccators and VAC Ovens.
3. Purge application bottle with $N_2$ for 10 seconds. Fill bottle with 60 ml of the enema composition via 100 ml granulated cylinder. Flush hood space with $N_2$ for 5 seconds. Cap bottle with pre-assembled tip.

Packaging/Pouching Matrix:
For purposes of comparison, the present study was conducted utilizing packages/pouches of the bottle enema composition in which the package/pouch configurations (1) received an oxygen ($O_2$) scavenging sachet (either large or small) and where sealed under nitrogen ($N_2$) atmosphere, or (2) received an oxygen scavenging sachet (either large or small), but were not sealed under nitrogen atmosphere, or (3) received no oxygen scavenging sachet, but were sealed under nitrogen atmosphere, or (4) received no oxygen scavenging sachet and were not sealed under nitrogen atmosphere. As described hereinabove, and with reference to the below study and results, it should be recognized and understood that under such nitrogen atmosphere conditions, the sealed package/pouch of the present invention preferably contain nitrogen gas therewithin.

The oxygen scavengers selected for the present study were the Multisorb Technologies, Inc.'s "large" oxygen scavenger (Frespax, D-200, part#02-01403CG05), and "small" oxygen scavenger (Freshpax, D-100, part#02-01403CG04).

TABLE 1

| Number of Packages/pouches | $N_2$ Present? | Small oxygen scavenger utilized? | Large oxygen scavenger utilized? | Package Configuration Reference Name (Sample I.D.) |
|---|---|---|---|---|
| 5 | No | No | No | A |
| 5 | No | — | Yes | B |
| 5 | Yes | No | No | C |
| 10 | Yes | Yes | — | D |
| 10 | Yes | — | Yes | E |

(Note: $O_2$ scavengers were placed on top of the application bottles while being pouched.)
Summary of Table 1:
A = 5 Pouches with no $N_2$ & no $O_2$ Scavenger
B = 5 Pouches with large $O_2$ Scavenger only
C = 5 Pouches with $N_2$ only.
D = 10 Pouches with $N_2$ & small $O_2$ Scavenger
E = 10 Pouches with $N_2$ & large $O_2$ Scavenger Stability Study and Analysis:
The stability study and analysis was conducted using the five (5) packaging configurations described above. The pouch "oxygen content" and appearance tests were performed to check the level of oxygen present, if any, in the packages/pouches, and to check the color of the enema compositions in the respective package configurations (i.e., color/appearance results represented in the tables below under "Pantone Color Code").

Each packaging configuration was placed on stability at 25° C./60% RH and 40° C./75% RH storage conditions (i.e., RH=relative humidity). All samples were stored horizontally in the stability chambers. The stability test stations included 2 weeks, 4 weeks, 1 M, and 3M (M=month/s), wherein the Tables 2-5, infra, provide the test results for same. The package configurations tested at particular time points were as follows:

| Test Station | Package Configurations Tested | Tests Performed |
|---|---|---|
| 2 Weeks | A, B, C, D, E | Pouch Oxygen Content, Enema Appearance |
| 4 Weeks | A, B, C, D, E | Pouch Oxygen Content, Enema Appearance |
| 1 Month | A, B, C, D, E | Pouch Oxygen Content, Enema Appearance |
| 3 Months | A, B, C, D, E | Pouch Oxygen Content, Enema Appearance |

The stability test results at the 2 week time point at 40° C./75% RH (i.e., under accelerated conditions) are depicted in Table 2 below. At the 2 week time point, and under such accelerated conditions, package configuration A (i.e., no nitrogen and no oxygen scavenger), and the enema composition thereof, failed (F=failed) the respective oxygen content and color (enema appearance) test, whereas package configurations B, C, D and E, and the enema compositions thereof, each met the established specifications for enema appearance and percent oxygen content tests (P=passed).

Significantly, however, package configurations D and E, which each contain nitrogen gas and an oxygen scavenger, and thus represent at least one preferred inventive packaging configurations for the sulfite-free/antioxidant-free 5-ASA enema composition of the present invention, exhibited 0.0% pouch oxygen content and met the established specifications for enema appearance (i.e., Pantone Color Code of 4675C (light)). Notably, package configurations B and C, which contain either nitrogen gas or an oxygen scavenger, but not both, each exhibited 0.6% pouch oxygen content. However, the enema composition of package configuration B (no nitrogen, but large oxygen scavenger) did exhibit better appearance than the enema composition of package configuration C (nitrogen, but no oxygen scavenger). As described supra, package configuration B represents the alternate embodiment comprising sealing of the package/pouch in the absence of a nitrogen atmosphere, but with the material inclusion of an oxygen scavenger.

in Table 3 below. At the 4 week time point, and under such accelerated conditions, package configuration A (i.e., no nitrogen and no oxygen scavenger), and the enema composition thereof, failed the respective oxygen content and color (enema appearance) test, whereas package configurations B, C, D and E, and the enema compositions thereof, each met the established specifications for enema appearance and percent oxygen content tests.

Yet again, package configurations D and E, which each contain nitrogen gas and an oxygen scavenger, and thus represent at least one preferred inventive packaging configurations for the sulfite-free/antioxidant-free 5-ASA enema composition of the present invention, exhibited 0.0% pouch oxygen content and met the established specifications for enema appearance (i.e., Pantone Color Code of 4685C (light)). Package configurations B and C, which contain either nitrogen gas or an oxygen scavenger, but not both, exhibited 0.0% and 0.4% pouch oxygen content, respectively. However, the enema composition of package configuration B (no nitrogen, but large oxygen scavenger) did exhibit better appearance than the enema composition of package configuration C (nitrogen, but no oxygen scavenger). Again, package

TABLE 2

Stability Condition: 40° C./75% RH (Accelerated)
Pull Station: 2 Weeks

| Sample ID | Packaging (Pouching) Configuration | Pouch Oxygen % | Pantone Color Code | Current Spec* | P/F |
|---|---|---|---|---|---|
| 1 | Un-pouched bottle on lab shelf | n/a | 4665c | NDT 4655C | P |
| A | No Nitrogen No Oxygen Scavenger | 14.1 | 4625c | NDT 4655C | F |
| B | No Nitrogen Large Oxygen Scavenger | 0.6 | 4685c | NDT 4655C | P |
| C | Nitrogen Purge No Oxygen Scavenger | 0.6 | 4665c | NDT 4655C | P |
| D | Nitrogen Purge Small Oxygen Scavenger | 0.0 | 4675c | NDT 4655C | P |
| E | Nitrogen Purge Large Oxygen Scavenger | 0.0 | 4675c | NDT 4655C | P |

*NDT: Not Darker Than

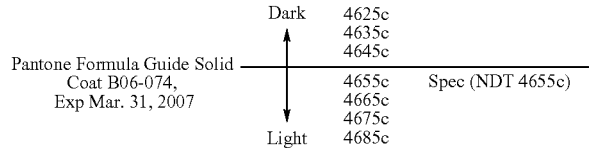

Sample I.D. #1 of Table 2 was an empty, unpouched application bottle, and was utilized as a control in the study.

The stability test results at the 4 week time point at 40° C./75% RH (i.e., under accelerated conditions) are depicted configuration B represents the alternate embodiment comprising sealing of the package/pouch in the absence of a nitrogen atmosphere, but with the material inclusion of an oxygen scavenger.

TABLE 3

Stability Condition: 40° C./75% RH (Accelerated)
Pull Station: 4 Weeks

| Sample ID | Packaging (Pouching) Configuration | Pouch Oxygen | Pantone Color | Current Spec* | P/F |
|---|---|---|---|---|---|
| 1 | Un-pouched bottle on lab shelf | n/a | 4655c | NDT 4655C | P |
| A | No Nitrogen No Oxygen Scavenger | 8.6 | 4625c | NDT 4655C | F |
| B | No Nitrogen Large Oxygen Scavenger | 0.0 | 4685c | NDT 4655C | P |

TABLE 3-continued

| | Stability Condition: 40° C./75% RH (Accelerated) Pull Station: 4 Weeks | | | | |
|---|---|---|---|---|---|
| Sample ID | Packaging (Pouching) Configuration | Pouch Oxygen | Pantone Color | Current Spec* | P/F |
| C | Nitrogen Purge No Oxygen Scavenger | 0.4 | 4665c | NDT 4655C | P |
| D | Nitrogen Purge Small Oxygen Scavenger | 0.0 | 4685c | NDT 4655C | P |
| E | Nitrogen Purge Large Oxygen Scavenger | 0.0 | 4685c | NDT 4655C | P |

*NDT: Not Darker Than

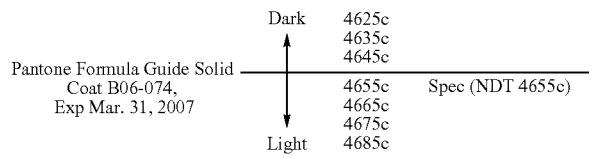

Sample I.D. #1 of Table 3 was an empty, unpouched application bottle, and was utilized as a control in the study.

The stability test results at the 1 month time point at 25° C./60% RH are depicted in Table 4 below. At the 1 month time point, package configuration A (i.e., no nitrogen and no oxygen scavenger), and the enema composition thereof, failed the respective oxygen content and color (enema appearance) test, whereas package configurations B, C, D and E, and the enema compositions thereof, each met the established specifications for enema appearance and percent oxygen content tests.

either nitrogen gas or an oxygen scavenger, but not both, exhibited 0.0% and 0.9% pouch oxygen content, respectively. However, the enema composition of package configuration B (no nitrogen, but large oxygen scavenger) again exhibited better appearance than the enema composition of package configuration C (nitrogen, but no oxygen scavenger). As indicated supra, package configuration B represents the alternate embodiment comprising sealing of the package/pouch in the absence of a nitrogen atmosphere, but with the material inclusion of an oxygen scavenger.

TABLE 4

| | Stability Condition: 25° C./60% RH Pull Station: 1 Month | | | | |
|---|---|---|---|---|---|
| Sample ID | Packaging (Pouching) Configuration | Pouch Oxygen % | Pantone Color Code | Current Spec* | P/F |
| A | No Nitrogen No Oxygen Scavenger | 16.8 | 4655c | NDT 4655C | F |
| B | No Nitrogen Large Oxygen Scavenger | 0.0 | 4675c | NDT 4655C | P |
| C | Nitrogen Purge No Oxygen Scavenger | 0.9 | 4675c | NDT 4655C | P |
| D | Nitrogen Purge Small Oxygen Scavenger | 0.0 | 4675c | NDT 4655C | P |
| E | Nitrogen Purge Large Oxygen Scavenger | 0.0 | 4675c | NDT 4655C | P |

*NDT: Not Darker Than

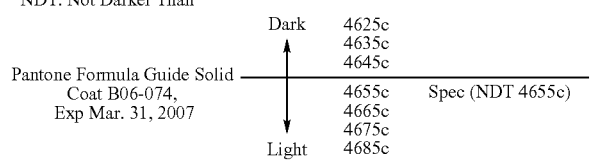

Once again, package configurations D and E, which each contain nitrogen gas and an oxygen scavenger, and thus represent at least one preferred inventive packaging configurations for the sulfite-free/antioxidant-free 5-ASA enema composition of the present invention, exhibited 0.0% pouch oxygen content and met the established specifications for enema appearance (i.e., Pantone Color Code of 4675C (light)). Package configurations B and C, which contain The stability test results at the 3 month time point at 25° C./60% RH are depicted in Table 5 below. At the 3 month time point, package configuration A (i.e., no nitrogen and no oxygen scavenger), and the enema composition thereof, failed the respective oxygen content and color (enema appearance) test, whereas package configurations B, C, D and E, and the enema compositions thereof, each met the established specifications for enema appearance and percent oxygen content tests.

Still again, package configurations D and E, which each contain nitrogen gas and an oxygen scavenger, and thus represent at least one preferred inventive packaging configurations for the sulfite-free/antioxidant-free 5-ASA enema composition of the present invention, exhibited 0.0% pouch oxygen content and met the established specifications for enema appearance (i.e., Pantone Color Code of 4685C (light)). Package configurations B and C, which contain either nitrogen gas or an oxygen scavenger, but not both, exhibited 0.0% and 0.5% pouch oxygen content, respectively. However, the enema composition of package configuration B (no nitrogen, but large oxygen scavenger) again exhibited better appearance than the enema composition of package configuration C (nitrogen, but no oxygen scavenger). Again, and as indicated supra, package configuration B represents the alternate embodiment comprising sealing of the package/pouch in the absence of a nitrogen atmosphere, but with the material inclusion of an oxygen scavenger.

TABLE 5

Stability Condition: 25° C./60% RH
Pull Station: 3 Months

| Sample ID | Packaging (Pouching) Configuration | Pouch Oxygen % | Pantone Color Code | Current Spec* | P/F |
|---|---|---|---|---|---|
| A | No Nitrogen No Oxygen Scavenger | 11.5 | 4625c | NDT 4655C | F |
| B | No Nitrogen Large Oxygen Scavenger | 0.0 | 4685c | NDT 4655C | P |
| C | Nitrogen Purge No Oxygen Scavenger | 0.5 | 4665c | NDT 4655C | P |
| D | Nitrogen Purge Small Oxygen Scavenger | 0.0 | 4685c | NDT 4655C | P |
| E | Nitrogen Purge Large Oxygen Scavenger | 0.0 | 4685c | NDT 4655C | P |

*NDT: Not Darker Than

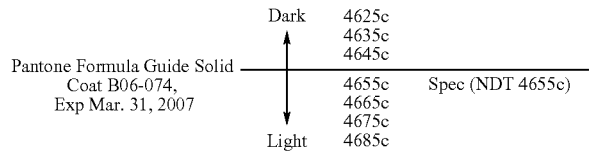

Pantone Formula Guide Solid Coat B06-074, Exp Mar. 31, 2007

Dark: 4625c, 4635c, 4645c
Spec (NDT 4655c): 4655c, 4665c, 4675c, 4685c
Light

Having thus described preferred and selective alternative embodiments of the present invention, it should be noted by those skilled in the relevant art that the within disclosures are exemplary only, and that various other alternatives, adaptations, and modifications may be made within the scope and spirit of the present invention. Accordingly, the present invention is not limited to the specific embodiments as illustrated herein, but is only limited by the following claims.

What is claimed is:

1. A packaged enema for the treatment of inflammatory bowel disease and related conditions, comprising:
   an effective and stable dosage suspension of substantially pure 5-ASA contained within a substantially oxygen-free liquid carrier medium, said liquid carrier medium having a material avoidance of antioxidants for said 5-ASA;
   at least one application bottle containing said effective dosage suspension;
   a sealed, substantially oxygen-free barrier package containing therein said at least one application bottle containing said effective dosage suspension, and an oxygen scavenger; and
   said barrier package sufficient to prevent migration of oxygen thereinto and to said dosage suspension upon prolonged storage.

2. The packaged enema of claim 1, wherein said sealed, substantially oxygen-free barrier package comprises a pouch.

3. The packaged enema of claim 1, wherein said at least one application bottle contained within a sealed oxygen barrier pouch is of sufficient flexibility to facilitate squeeze dispensing of the contents thereof.

4. The packaged enema of claim 1, wherein said oxygen scavenger is contained within said oxygen barrier package.

5. The packaged enema of claim 1, wherein said oxygen scavenger is contained within a sachet.

6. The packaged enema of claim 1, wherein said application bottle is formed from a malleable polymer.

7. The packaged enema of claim 1, wherein said oxygen barrier package comprises a laminate comprising polyester/aluminum foil/linear low density polyethylene.

8. The packaged enema of claim 7, wherein said laminate further comprises at least one compatible adhesive.

9. The packaged enema of claim 1, wherein said oxygen scavenger is disposed within said sealed substantially oxygen-free barrier package in substantially isolated disposition with regard to said stable dosage suspension.

10. The packaged enema of claim 1, wherein said oxygen scavenger is disposed within said sealed substantially oxygen-free barrier package in substantially communicating disposition with regard to said stable dosage suspension.

11. The packaged enema of claim 1, wherein said effective dosage amount is approximately 1 g. to approximately 4 g. of 5-ASA disposed within approximately 20 to approximately 60 ml of said liquid carrier medium.

12. The packaged enema of claim 1, wherein said liquid carrier medium comprises potassium acetate, xanthan gum, carbomer, sodium benzoate, edentate disodium and purified water.

13. The packaged enema of claim 1, wherein said package contains a substantially inert gas.

14. The packaged enema of claim 13, wherein said substantially inert gas comprises nitrogen.

15. The packaged enema of claim 1, wherein said application bottle contains a substantially inert gas.

16. The packaged enema of claim 15, wherein said substantially inert gas comprises nitrogen.

17. The packaged enema of claim 1, wherein said effective dosage has a pH of approximately 3 to approximately 5.

18. The packaged enema of claim 1, wherein said barrier package is further sufficient to prevent discoloration of said dosage suspension upon prolonged storage.

\* \* \* \* \*